(12) United States Patent
Grange et al.

(10) Patent No.: US 8,257,532 B2
(45) Date of Patent: Sep. 4, 2012

(54) METHOD FOR PRODUCING A DEVICE FOR PROTECTING AN AREA OF THE HUMAN BODY

(75) Inventors: Odile Grange, Allex (FR); Damien Millet, Valence (FR)

(73) Assignee: Millet Innovation, Loriol sur Drôme (FR)

( * ) Notice: Subject to any disclaimer, the term of this patent is extended or adjusted under 35 U.S.C. 154(b) by 0 days.

(21) Appl. No.: 13/197,831

(22) Filed: Aug. 4, 2011

(65) Prior Publication Data

US 2012/0018076 A1    Jan. 26, 2012

Related U.S. Application Data

(63) Continuation of application No. PCT/IB2010/000033, filed on Jan. 6, 2010.

(30) Foreign Application Priority Data

Feb. 13, 2009    (FR) ..................................... 09 00665

(51) Int. Cl.
*B32B 31/18*    (2006.01)
(52) U.S. Cl. ........ 156/145; 156/250; 156/251; 156/197; 156/289; 156/249; 156/247; 156/297; 156/298; 156/300
(58) Field of Classification Search .................. 156/145, 156/250, 251, 197, 289, 249, 247, 297, 298, 156/300
See application file for complete search history.

(56) References Cited

U.S. PATENT DOCUMENTS

| 5,670,232 | A | 9/1997 | Bigolin |
| 6,309,500 | B1 * | 10/2001 | Jensen et al. ................... 156/247 |
| 2002/0095107 | A1 | 7/2002 | Martin |
| 2008/0262403 | A1 | 10/2008 | Martin |

FOREIGN PATENT DOCUMENTS

| FR | 2793678 A1 | 11/2000 |
| FR | 2892298 A1 | 4/2007 |
| WO | 0071066 A1 | 11/2000 |
| WO | 0174566 A1 | 10/2001 |
| WO | 2007045737 A2 | 4/2007 |
| WO | 2008128206 A1 | 10/2008 |

OTHER PUBLICATIONS

Int'l Preliminary Report on Patentability issued Aug. 16, 2011 in Int'l Application No. PCT/IB2010/000033; Written Opinion.
Int'l Search Report and Written Opinion issued Apr. 8, 2010 in Int'l Application No. PCT/IB2010/000033.

* cited by examiner

*Primary Examiner* — Jeff Aftergut
*Assistant Examiner* — Jaeyun Lee
(74) *Attorney, Agent, or Firm* — Panitch Schwarze Belisario & Nadel LLP

(57) ABSTRACT

A method for manufacturing a protection device includes the steps of forming a plurality of cells in a support strip, filling the cells with a non-cross-linked compound, cross-linking the compound to form at least one module made of viscoelastic gel in the plurality of cells, depositing an adhesive substance on each module, and depositing a strip of fabric on the support strip to obtain a final compound strip. The at least one module made of viscoelastic gel is glued onto the strip of fabric by the adhesive substance.

14 Claims, 4 Drawing Sheets

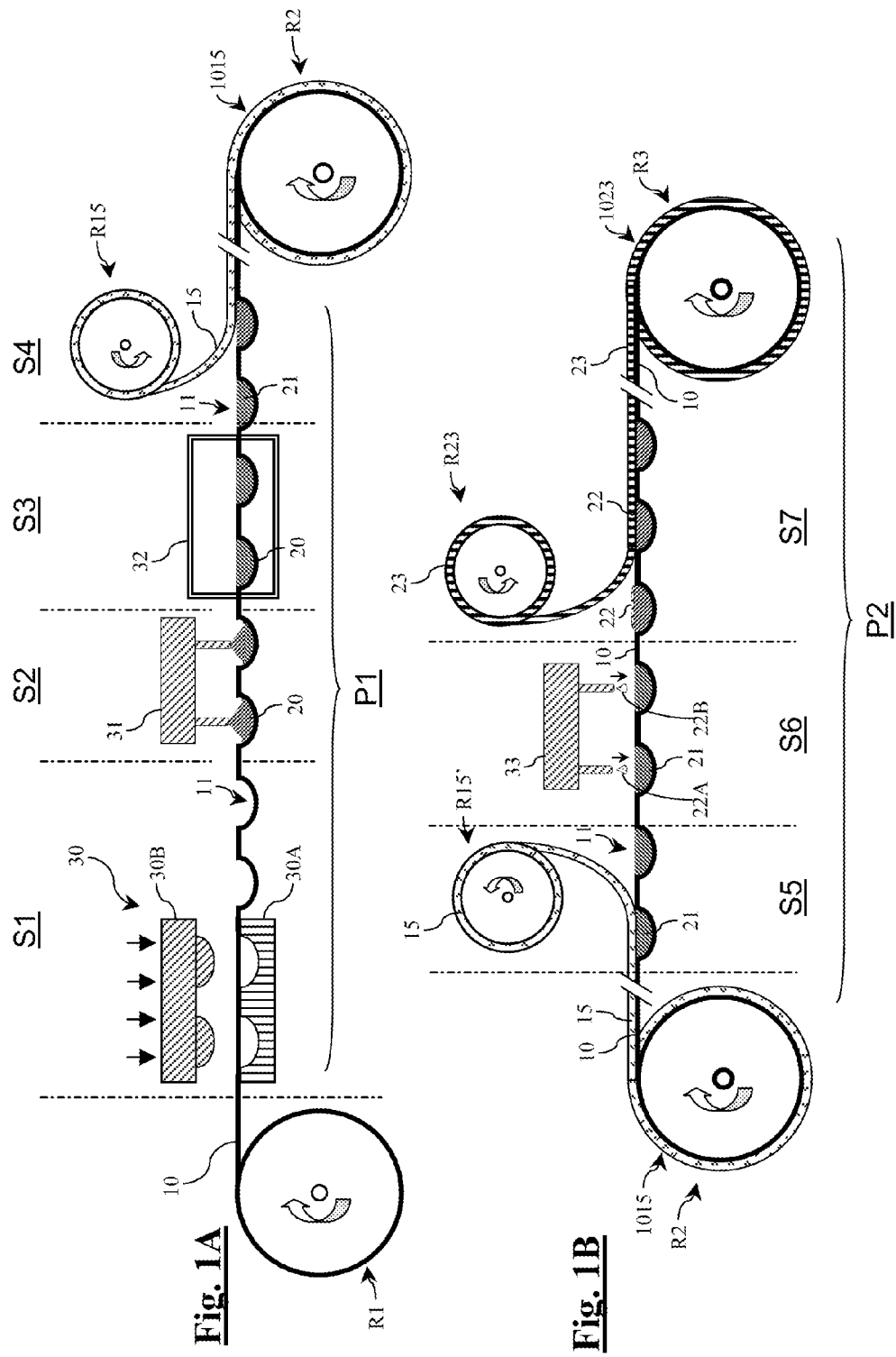

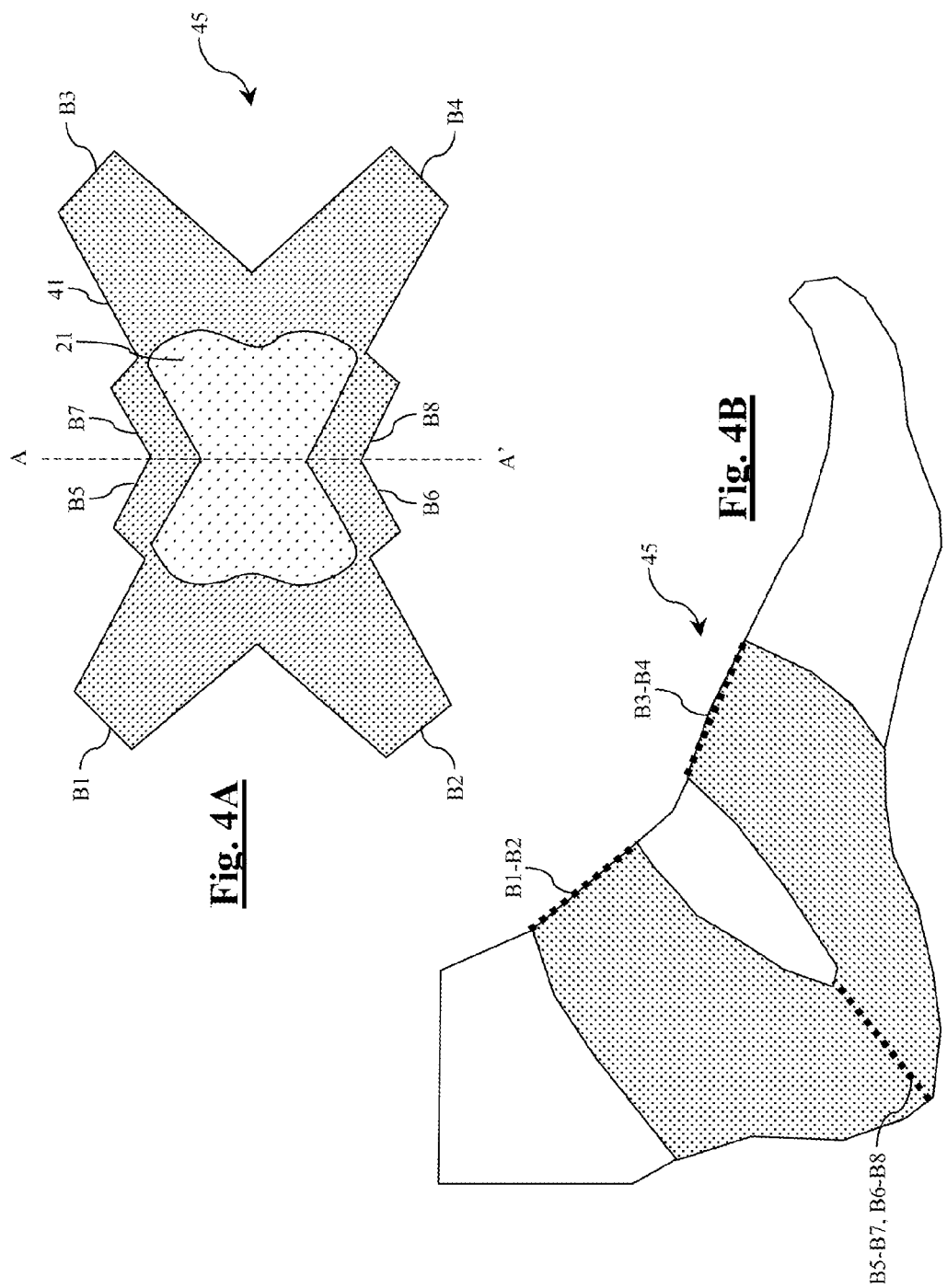

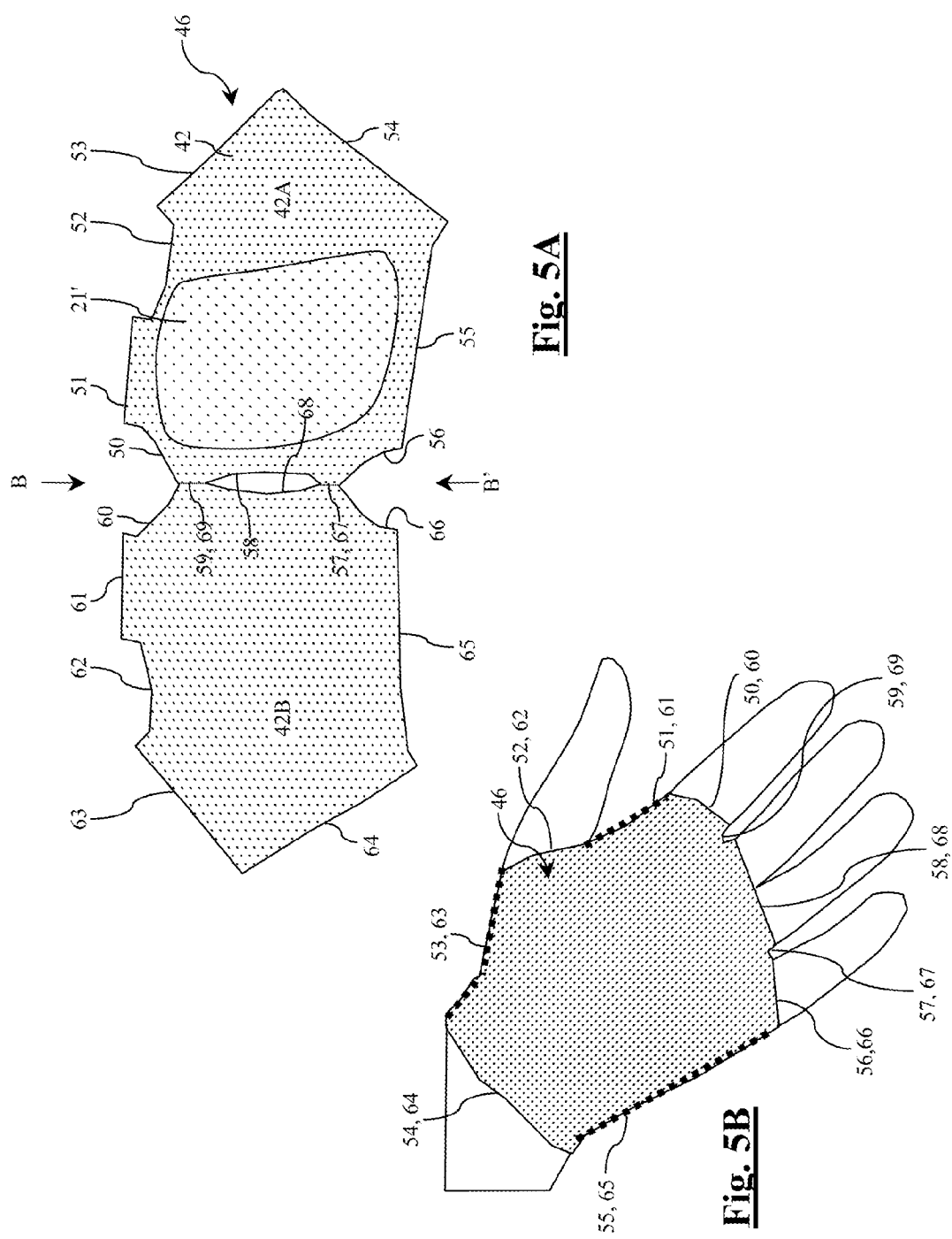

METHOD FOR PRODUCING A DEVICE FOR PROTECTING AN AREA OF THE HUMAN BODY

CROSS-REFERENCE TO RELATED APPLICATIONS

This application is a Continuation of International Application No. PCT/IB2010/000033, filed Jan. 6, 2010, which was published in the French language on Aug. 19, 2010, under International Publication No. WO 2010/092445 A1 and the disclosure of which is incorporated herein by reference.

BACKGROUND OF THE INVENTION

A preferred embodiment of the present invention relates to a method for manufacturing a protection device comprising a piece of fabric and a module made of viscoelastic gel glued onto the piece of fabric.

Protection devices of the above-mentioned type are generally designed to protect areas of the human body, for example areas with bedsores, blisters, chaps, or to protect healthy areas against shocks, heating due to friction, etc. They are generally washable and reusable.

A traditional method for manufacturing a protection device of the above-mentioned type generally comprises the following steps:
  depositing a cross-linkable compound in a mold,
  cross-linking the compound to obtain a module made of viscoelastic gel,
  unmolding the module,
  cutting a piece of fabric,
  gluing the module onto the piece of fabric, and
  optionally, sewing or binding the edges of the piece of fabric, to form an orthosis which can be pulled onto the area of the body to be protected (hand, foot, arm, leg, etc.).

This manufacturing method generally comprises manual steps, because the gelatinous texture of the modules made of viscoelastic gel renders them unfit for handling by machines. The cross-linking time of viscoelastic gels represents an additional constraint preventing large-scale manufacturing.

Some steps of this method can be streamlined as part of industrial production, for example by simultaneously producing a plurality of modules made of viscoelastic gel in molds with multiple cavities. However, automating the steps of unmolding, transporting and then gluing the modules onto the pieces of fabric remains difficult.

It can therefore be desired to provide a manufacturing method whereby the cost price of such devices can be significantly reduced, by streamlining the steps of manufacturing and gluing the modules made of viscoelastic gel onto pieces of fabric.

International applications WO 2000/71066 and WO 2007/045737 describe methods for manufacturing protection devices of the above-mentioned type. They provide for covering a strip of fabric with a layer of viscoelastic gel also in strip form. The strip of fabric is then pulled down edge to edge longitudinally, and the opposite edges are sewn or bound. The strip is then cut into sections of determined lengths to form protective sleeves for the fingers or toes, called "digitubes" (registered trademark). Such manufacturing methods thus relate specifically to the manufacturing of protective sleeves and cannot be used generally to industrially manufacture protection devices of any form.

BRIEF SUMMARY OF THE INVENTION

Some preferred embodiments of the present invention relate to a method for collectively manufacturing a protection device comprising a piece of fabric and a module made of viscoelastic gel glued onto the piece of fabric, comprising the steps of forming a plurality of cells in a support strip made of a deformable material, filling the cells with a non-cross-linked compound, cross-linking the compound to obtain modules made of viscoelastic gel in the cells, depositing on each module an adhesive substance, and depositing a strip of fabric on the support strip to obtain a final compound strip in which the modules made of viscoelastic gel present in the cells are glued to the strip of fabric by the adhesive substance.

According to one preferred embodiment, the method comprises, between the steps of forming the modules and of depositing an adhesive substance on the modules, the steps of depositing a protective film on the support strip to obtain an intermediate compound strip in which the modules made of viscoelastic gel present in the cells are covered by the protective film, and winding the intermediate compound strip so as to form a roll of intermediate compound strip.

According to one preferred embodiment, the protective film is deposited on the support strip before the compound in the cells is entirely cross-linked, and the method comprises a step of storing the roll of intermediate compound strip during which the cross-linking of the compound can continue.

According to one preferred embodiment, the method comprises, before the step of depositing the adhesive substance on the modules made of viscoelastic gel, a step of unwinding the roll of intermediate compound strip and of removing the protective film.

According to one preferred embodiment, the method comprises a step of forming a roll with the final compound strip.

According to one preferred embodiment, the adhesive substance is a polymerizable glue, and the method comprises a step of storing the roll of final compound strip during which the adhesive substance polymerizes or continues to polymerize.

According to one preferred embodiment, the method comprises a step of separating the support strip from the strip of fabric without unsticking the modules made of viscoelastic gel from the strip of fabric.

According to one preferred embodiment, the method comprises a step of cutting the strip of fabric to obtain a piece of fabric comprising at least one module made of viscoelastic gel.

According to one preferred embodiment, the method comprises a step of folding the piece of fabric according to a folding axis, and steps of sewing or binding edges of the piece of fabric to form a protection device which can be slipped onto a part of the human body.

According to one preferred embodiment, the method is applied to the manufacturing of a protection device for protecting the foot, and comprises: a step of cutting out of the strip of fabric a piece of fabric comprising four large branches, including two on the left of a folding axis and two on the right of the folding axis, between two large branches, two small truncated branches arranged on the left and right of the folding axis and towards the folding axis, comprising two edges joining on the folding axis, and between two other large branches, two small truncated branches arranged on the left and right of the folding axis and towards the folding axis, comprising two edges joining on the folding axis; a step of folding the piece of fabric so that the small branches are superimposed; and a step of sewing or binding the small superimposed branches, to form a module for protecting the heel, the large branches being intended to be linked in pairs by connection means, to form straps for holding the heel protection module.

According to one preferred embodiment, the method is applied to the manufacturing of a protection device for protecting the hand and comprises: a step of cutting out of the strip of fabric a piece of fabric having two symmetrical parts in relation to a folding axis; a step of folding the piece of fabric so that the two parts are one above the other; and a step of sewing or binding to link in pairs the superimposed edges of the two parts, such that the device has edges not sewn or bound forming openings enabling the wrist and fingers to be passed through it.

According to one preferred embodiment, the support strip is made of polyvinyl chloride.

According to one preferred embodiment, the modules are made of silicone gel.

According to one preferred embodiment, the fabric is elastane polyamide.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 1A is a cross-sectional schematic view showing steps of a manufacturing method according to a preferred embodiment of the present invention;

FIG. 1B a cross-sectional schematic view showing steps of a manufacturing method according to a preferred embodiment of the present invention;

FIG. 4A represents an example of protection device in a non-assembled form;

FIG. 4B represents an example of protection device in an assembled form;

FIG. 5A represents another example of a protection device in a non-assembled form; and FIG. 5B represents another example of a protection device in an assembled form.

DETAILED DESCRIPTION OF THE INVENTION

Figure 2A:
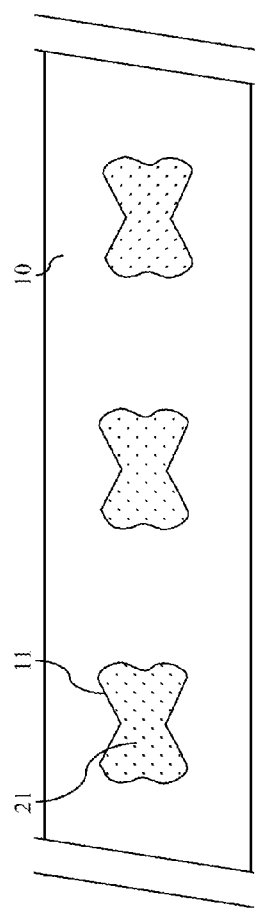
FIG. 2A is a top view of a support strip after a step S2 represented in FIG. 1A.

FIGS. 1A and 1B represent steps of one preferred embodiment of a method for collectively manufacturing protection devices according to the present invention. The method comprises phases P1, P2 and P3. The phase P1, shown in FIG. 1A, comprises steps of forming modules made of viscoelastic gel 21 in cells 11 of a support strip 10. The phase P2, shown in FIG. 1B, comprises a step of gluing the modules 21 onto a strip of fabric 23, without extracting the modules from the cells 11. The phase P3 comprises a step of separating the support strip 10 from the strip of fabric 23, without unsticking the modules 21, and a step of cutting the strip of fabric to obtain non-assembled protection devices.

Phase P1 is implemented on a first manufacturing line schematically represented in FIG. 1A. At a first end of the manufacturing line a roll R1 of the support strip 10 is arranged. According to one preferred embodiment, the support strip 10 is made of thermoplastic polymer, for example PVC (polyvinyl chloride). It has for example a thickness in the order of 1 to 2 tenths of a millimeter. The roll R1 is unwound step by step and processing steps S1 to S4 are applied to the support strip 10 as it advances. A second roll R2 is formed with the support strip 10, at the other end of the manufacturing line.

In the step S1, a portion of the support strip 10 is hot deformed by a tool 30, so as to form the above-mentioned cells 11. According to one preferred embodiment, the tool 30 is a thermoforming machine which comprises a lower part 30A and an upper part 30B. The part 30A comprises negative impressions in the form of cells and the part 30B comprises positive impressions the form of which corresponds to that of the cells of the negative impression. In one alternative preferred embodiment, a suction system can also be used to thermoform the support strip in a negative impression having the desired shape.

Every time the support strip 10 advances step by step, a new group of cells 11 is formed. Downstream from the thermoforming machine, the support strip 10 has a continuous series of cells 11 arranged in series in the unwinding direction of the support strip. The spacing between the cells is chosen according to the shape and the size of the protection devices to be produced, examples of which will be described below.

To simplify the drawing, the machine 30 represented in FIG. 1A comprises only two cells. In practice, a higher number of cells can be produced simultaneously. Moreover, in addition to forming cells 11 in series in the unwinding direction of the support strip, the machine 30 could be made such that it can also produce cells in parallel relative to the unwinding direction of the support strip. This may be the case for example when protection devices to be produced must comprise two modules of viscoelastic gel, or more, arranged side by side. However, modules intended to be integrated into the same protection device could also be arranged in series on the strip.

In the step S2, the cells 11 pass beneath a metering distributor 31 comprising one or more nozzles for dispensing a cross-linkable compound 20. The compound 20 is deposited in the cells 11, each dispensing nozzle filling one cell. The compound is for example a fluid mixture of cross-linkable silicone oils.

In the step S3, the cells 11 filled with the cross-linkable compound 20 go through a heated tunnel 32 to cross-link the compound 20. The temperature in the heated tunnel is for example in the order of 40 to 65° C. The duration of the process is for example of a few minutes. When exiting the heated tunnel, the compound 20 is at least partially cross-linked and the cells 11 thus contain the above-mentioned modules made of viscoelastic gel 21, for example silicone gel. As an example, FIG. 2A is a top view of the support strip 10 and of the cells 11 containing the modules 21.

In the step S4, a protective film 15 is applied without gluing onto the support strip 10, so as to cover the modules 21. The protective film 15 is, for example, supplied by a roll R15 which is unwound step by step in synchronization with the advance of the support strip. The film 15 naturally but not excessively adheres to the modules 21. The film 15 is for example a polyethylene film of the type used in the food industry. An intermediate compound strip 1015 is thus obtained comprising the support strip 10 and the film 15, in which the modules 21 present in the cells are covered by the film 15. The compound strip 1015 is rolled around a spindle to form the roll R2, which can be stored pending the phase P2. Therefore, if the modules 21 are not fully cross-linked when the roll R2 is formed, they can continue to cross-link at ambient temperature during the storage of the roll R2. Storage at forced temperature can also be considered, according to the targeted production rates and the storage means available.

As indicated above, the phase P1 is implemented on a step-by-step basis and the unwinding of the support strip 10 is stopped at each step of thermoforming S1, filling S2, and heating S3. The steps S1, S2, S3 can be initiated simultaneously as they are applied to different portions of the support strip, the longest step to be carried out requiring the step-by-step strip unwinding speed. Those skilled in the art will have to optimize each step so that the strip unwinding speed is maximized or adapted to the desired production pace. In particular, the fact of only aiming for partial cross-linking of the modules 21 during step S3 avoids penalizing the support strip unwinding speed. As an example, the average support strip unwinding speed 10 (including breaks) can be typically in the order of 0.5 to 2 meters per minute.

The phase P2 is implemented in a second manufacturing line schematically represented in FIG. 1B. The roll R2 of intermediate compound strip 1015 is arranged at a first end of the second manufacturing line. The roll R2 is unwound and processing steps S5 to S7 are applied to the support strip 10 as it advances. A third roll R3 is formed with the support strip 10, at the other end of the second manufacturing line.

In the step S5, the protective film 15 is removed from the support strip 10. The film 15 is for example rolled around a spindle to form a roll R15' which could then be recycled. The upper face of the modules 21 in the cells 11 is thus again exposed to the air.

In the step S6, the modules 21 pass beneath a metering distributor 33 comprising one or more dispensing nozzles by means of which a polymerizable glue 22 is deposited on the modules 21. The glue 22 is for example formed by two fluid components 22A, 22B each dispensed by a nozzle of the metering distributor, which polymerize when they are in contact. A thin film of glue 22 is thus deposited on the modules 21. In one alternative preferred embodiment of step S6, a single-component glue is supplied by a single nozzle of the metering distributor and is then spread over the surface of the modules 21 by means of coating rollers ensuring rolling contact on the modules 21 with application of slight pressure. In another alternative preferred embodiment, a machine deposits on the surface of each module 21 an adhesive film 22 which is adhesive on its two faces. Unlike the phase P1, the phase P2 can be implemented with continuous unwinding of the support strip 10, the step of depositing the glue 22 not requiring the support strip to be stopped.

Figure 2B:
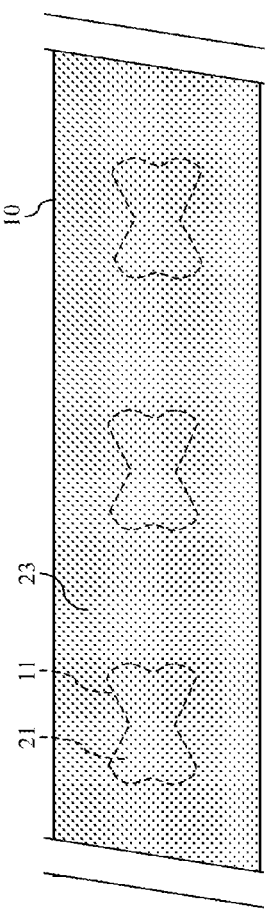
FIG. 2B is a top view of the support strip after a step S7 represented in FIG. 1B.

In the step S7, the above-mentioned strip of fabric 23 is applied onto the support strip 10. The strip of fabric 23 is for example supplied by a roll R23 which is unwound in synchronization with the advance of the support strip. The fabric 23 is for example an elastane polyamide. At the time of applying the strip of fabric 23 onto the support strip 10, the modules 21 stick to the fabric 23 thanks to the thin layer or film of glue 22, without the fabric sticking to the support strip 10. A final compound strip 1023 is thus obtained comprising the support strip 10 and the fabric 23, in which the modules 21 present in the cells are glued to the fabric 23. As an example, FIG. 2B shows by a top view the appearance of the support strip 10 covered by the fabric 23. The cells 11 and the modules 21 are beneath the fabric 23 and are represented in dotted lines.

The compound strip 1023 is wound up to form the roll R3, which can be stored for phase P3. It shall be noted that, like for the viscoelastic gel 20, when the roll R2 is formed, the glue 22 may not be completely polymerized when the roll R3 is formed. The glue 22 can continue to polymerize at ambient or forced temperature during storage of the roll R3.

Figure 3A:
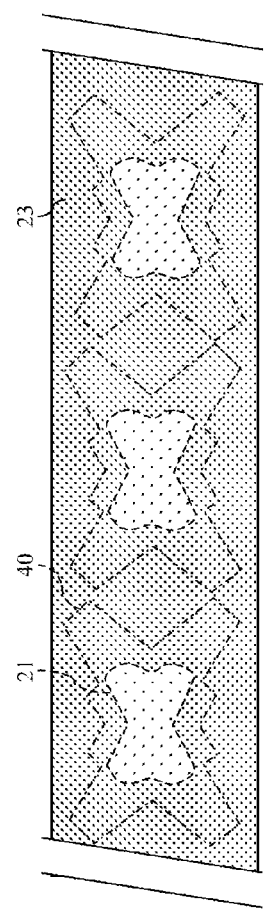
FIG. 3A is a top view of a strip of fabric comprising modules made of viscoelastic gel, produced by means of the aforementioned method.
Figure 3B:
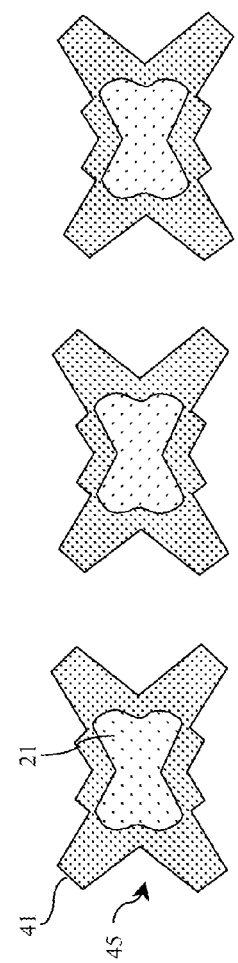
FIG. 3B represents the strip of fabric after the latter has been cut, so as to obtain non-assembled protection devices.

During the phase P3, the roll R3 is unwound and the support strip 10 is separated from the strip of fabric 23 to obtain a strip of fabric 23 on which the modules 21 are glued, as shown in FIG. 3A. The strip of fabric 23 is then cut according to a determined pattern 40 to obtain pieces of fabric 41 of the type represented in FIG. 3B, each comprising at least one module made of viscoelastic gel 21. Each piece of fabric 41 and its module 21 form a non-assembled protection device 45. In one alternative preferred embodiment, the strip of fabric 23 is cut before removing the support strip 10. The separation from the support strip is then done piece by piece.

The phase P3 can be automated or manual. It can be executed for example by a separation machine which winds the support strip 10 around a spindle to form a recyclable roll, and which then cuts the fabric, for example by means of a laser beam.

In one alternative preferred embodiment of the phase P3, the separation and cutting machine is arranged in line with the machines used to implement the phase P2. In this case, it is not necessary to form the roll R3. In another alternative preferred embodiment, the roll R3 is delivered to an assembling shop which extracts the modules from the cells by unwinding the strip of fabric 23 on which the modules are glued, and cuts the strip of fabric.

The phase P3 can be followed by an assembly phase P4. "Assembly" here means the fact of conducting steps of sewing or binding certain edges of the pieces of fabric 41, to form assembled protection devices which can be slipped onto the areas of the body to be protected.

FIGS. 4A and 4B represent, respectively, in a non-assembled and assembled form, an example of one preferred embodiment of a protection device 45 which can be manufactured according to the method that has just been described. The device 45 is provided to protect the heel and enables for example inflammatory pathologies or hyperkeratosis causing chapping to be treated. It comprises a piece of fabric 41 and a module 21 made of viscoelastic gel the shape of which resembles two butterfly wings. According to one preferred embodiment, the module 21 is made of a silicone gel which is very adhesive to the skin.

The butterfly wings shape of the module 21 is thus chosen to thermoform the cells of the support strip during step S1 of the phase P1 (FIG. 1A). The module 21 is continuously poured into the cells, as indicated, and is then transferred and glued onto the strip of fabric 23 during the step S7 of the phase P2 (FIG. 1B). The strip of fabric is then cut according to the shape represented in FIG. 4A (or FIG. 3A). More particularly, the piece of fabric here has a symmetrical star shape along a folding axis AA' which comprises:

- four large truncated branches B1, B2, B3, B4 arranged substantially as a cross, two of them B1, B2 being arranged on the left of the axis AA' and two others B3, B4 being arranged on the right of the axis AA',
- between the truncated branches B1, B3, two small truncated branches B5, B7 directed towards the axis AA' the ends of which form two edges joining on the axis AA', one on the left of the axis AA' and the other on the right of the axis AA', the two small branches together forming an edge substantially in the shape of an inverted "W",
- between the branches B2, B4, two small truncated branches B6, B8 directed towards the axis AA' but in the opposite direction to the branches B5, B7, the ends of which form two edges joining on the axis AA', one on the left of the axis AA' and the other on the right of the axis AA', the two small branches together forming an edge substantially in the shape of a "W".

The assembly of the protection device 45 first of all comprises a step of folding the fabric 41 along the axis AA', then steps of sewing or binding the ends of the branches B5 and B7, B6 and B8 near their edges, for example at about 1 mm from the module 21. If binding is performed, the excess fabric of the branches can be removed during the operation. If sewing is performed, the excess can be removed by cutting it off.

The device can then be finalized according to two preferred embodiments. In a first preferred embodiment, the end of the branch B1 is sewn or bound to the end of the branch B2 and the end of the branch B3 is sewn or bound to the end of the branch B4. Once the device is pulled around the foot, as represented in FIG. 4B, the seam or binding B1-B2 extends onto the lower part of the tibia, the seam or binding B3-B4 extends onto the arch of the foot, and the seams or bindings B5-B7 and B6-B8 surround the heel.

In a second preferred embodiment, the branches B1, B2, B3, B4 are provided substantially longer and are not sewn or bound. The user can then tie the ends of the branches B1 and B2 and the ends of the branches B3 and B4. Other means of connecting the ends of the branches B1, B2 and B3, B4 could also be considered, such as a Velcro®-type material for example.

In summary, the sewn or bound area of the fabric which includes the module 21 forms a shell for protecting the heel, and the device 45 has two holding straps formed by the large branches of the piece of fabric which can be sewn, bound, or attached by a temporary connection means, or even tied by the user.

Such a protection device structure enables an excellent hold of the rest area of the heel and the two straps ensure a stable and balanced hold of the device. The symmetry of the device also avoids having to produce one device for left feet and one device for right feet.

FIGS. 5A and 5B represent, respectively, in a non-assembled and assembled form, another example of a protection device 46 which can be manufactured according to the method described above. The device 46 is provided to protect the palm of the hand. It comprises a piece of fabric 42 and a module 21' made of viscoelastic gel glued onto the piece of fabric. The module 21' here has a quadrilateral shape with rounded angles, substantially corresponding to the shape of the palm of the hand. The piece of fabric 42 is cut so as to have two symmetrical parts 42A, 42B in relation to a folding axis BB'. The part 42A, on the right of the axis BB' in FIG. 5A, receives the module 21' and has edges 50, 51, 52, 53, 54, 55, 56, 57, 58, 59. The part 42B is the image of the part 42A in relation to the axis BB' as axis of symmetry and has edges 60, 61, 62, 63, 64, 65, 66, 67, 68, 69. The edges 57 and 67, and the edges 59 and 69 are joined and aligned with the axis BB', the piece of fabric 42 not being cut along these edges. Thus, the edges 57 and 67, 59 and 69 connect the parts 42A, 42B before sewing or binding them. The edges 58, 68 are obtained by cutting a slit along the axis BB', between the edges 57, 67 and the edges 59, 69.

The assembly of the device 46 comprises a step of folding the piece 42 in relation to the axis BB', so that the parts 42A, 42B are one above the other, and steps of sewing or binding the edges 51 and 61, 53 and 63, 55 and 65. The device can then be pulled around the hand as represented in FIG. 5B. The edges not sewn 54, 64 form an opening enabling the wrist to pass, the edges not sewn 52, 62 form an opening enabling the thumb to pass, the edges not sewn 50, 60 form an opening enabling the forefinger to pass, the edges not sewn 58, 68 form an opening enabling the middle finger and the ring finger to pass, and the edges not sewn 56, 66 form an opening enabling the little finger to pass.

The pain to be treated mentioned above for the protection of the heel can also concern the hand and warrant using the protection device 46. The latter can also be used, for example, when playing sports or for gardening activities. Therefore, once again, a simple folding and a few sewing or binding steps enable a flat object to be transformed into a three-dimensional product well adapted to the protection of the targeted area of the body.

Although the method described above is well suited to industrial manufacturing of the protection devices 45, 46, it will be noted that each of these devices also forms, as such, an innovative object independent of their manufacturing method.

Other preferred embodiments of the manufacturing method according to the present invention can enable other types of modules made of viscoelastic gel to be produced, concerning other parts of the body. The difference between a method according to the present invention, wherein the step of sewing or binding the fabric is conducted after cutting the fabric, and a method of the type described by applications WO 2000/71066 and WO 2007/045737, wherein the step of sewing or binding is on the contrary conducted before cutting the fabric, shall be noted. Another difference lies in the fact that the module made of viscoelastic gel is in the form of a continuous strip in the Digitubes® according to WO 2000/71066 and WO 2007/045737, whereas a method according to the present invention makes it possible to produce distinct modules thanks to the cells formed in the support strip.

It will be understood by those skilled in the art that various other preferred embodiments of the manufacturing method according to the present invention can be provided. For example, materials other than PVC could be used to form the support strip 10. The thermoplastic material forming the support strip must preferably have all or part of the following properties:

appropriate wettability, so that the liquid compound 20 is correctly distributed in the cells during the step S2, good temperature resistance to go through the heated tunnel 32 without deforming, good mechanical flexibility to wind up without creasing during the formation of the roll R2 or R3, low relative adhesiveness of the viscoelastic gel in the cells 11, so that the force required to extract the modules 21 from the cells 11 is low enough so as not to unstick the modules 21 from the strip of fabric 23, and good neutrality in relation to the cross-linking process. Thus, for example, a material like polyester can inhibit the cross-linking process of certain silicone oils.

Furthermore, using a cold-deformable material to produce the support strip and its cells could be considered.

Those skilled in the art will also note that the phases P1 and P2 shown in FIGS. 1A and 1B could be implemented in a single manufacturing line. In such a preferred embodiment, the protective film 15 would not be necessary, nor the formation of the roll R2. The fact that the phases P1, P2 are not implemented in a same manufacturing line however offers benefits relating to the cross-linking time of the gel. Thus, forming a roll R2 with the support strip 10 enables the latter to be stored until the modules 21 are completely cross-linked, as already indicated. It is simply necessary, at the end of step S3, that the modules 21 be sufficiently cross-linked to be covered by the protective film 15, but it is not necessary for them to be entirely cross-linked. Their cross-linking can continue for several hours, during the storage of the rolls R2. On the contrary, it is preferable that the modules 21 be entirely cross-linked before undergoing the gluing step S7. Therefore, putting the phases P1, P2 in line requires the heated tunnel 32 to be extended (at a constant manufacturing rate) to obtain the full cross-linking of the modules before the gluing step S7, which involves higher power consumption to compensate for the cross-linking time available in the case of storing the roll R2.

In addition to the gain in power consumption, separating the phases P1, P2 into two different manufacturing lines may offer other benefits. For example, it is not necessary for the two manufacturing lines to have the same strip unwinding speed and the same unwinding mode of the support strip (step by step for the phase P1 and continuous for the phase P2). Also, the gluing machine 33 can be used for other applications during the manufacturing of rolls R2 and their storage.

Some preferred embodiments of the method of manufacturing according to the present invention have been initially designed to produce protection devices for protecting areas of the human body. However, it goes without saying that the present invention is not limited to this application. Some preferred embodiments of the present invention can for example be provided to produce protection devices for protecting the animal body or even devices intended to be arranged on inert objects.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method for manufacturing a protection device comprising a piece of fabric and at least one module comprising viscoelastic gel, the module being glued onto the piece of fabric, the method comprising the steps of:
    forming a plurality of cells in a support strip comprising a deformable material,
    filling the plurality of cells with a non-cross-linked compound,
    cross-linking the compound to form the at least one module comprising viscoelastic gel in the plurality of cells,
    depositing an adhesive substance on each module, and
    depositing a strip of fabric on the support strip to obtain a final compound strip in which the at least one module comprising viscoelastic gel in the plurality of cells is glued to the strip of fabric by the adhesive substance.

2. The method according to claim 1 further comprising, between the steps of forming the at least one module and of depositing the adhesive substance on each module, the steps of:
    depositing a protective film on the support strip to obtain an intermediate compound strip in which the at least one module is covered by the protective film; and
    winding the intermediate compound strip so as to form a roll of the intermediate compound strip.

3. The method according to claim 2, wherein the protective film is deposited on the support strip before the compound in the cells is entirely cross-linked, the method further comprising a step of storing the roll of the intermediate compound strip during which step the cross-linking of the compound can continue.

4. The method according to claim 2 further comprising, before the step of depositing the adhesive substance on each module, a step of unwinding the roll of the intermediate compound strip and of removing the protective film.

5. The method according to claim 1 further comprising a step of forming a roll with the final compound strip.

6. The method according to claim 5, wherein the adhesive substance is a polymerizable glue, the method further comprising a step of storing the roll of the final compound strip during which step the adhesive substance polymerizes or continues to polymerize.

7. The method according to claim 1 further comprising a step of separating the support strip from the strip of fabric without unsticking the at least one module from the strip of fabric.

8. The method according to claim 7 further comprising a step of cutting the strip of fabric to obtain a piece of fabric comprising the at least one module.

9. The method according to claim 8 further comprising the steps of:
    folding the piece of fabric according to a folding axis; and
    sewing or binding edges of the piece of fabric to form a protection device which is configured to be slipped onto a part of the human body.

10. The method according to claim 8 for manufacturing a protection device, the protection device being configured to protect a foot, the method further comprising the steps of:
    cutting out of the strip of fabric a piece of fabric comprising four large branches and four small truncated branches, two of the large branches being on a left of a folding axis and another two of the large branches being on a right of the folding axis, two of the small truncated branches being arranged on the left and right of the folding axis proximate to the folding axis between two of the large branches and comprising two edges joining on the folding axis, and another two of the small truncated branches being arranged on the left and right of the folding axis proximate to the folding axis between another two of the large branches and comprising two edges joining on the folding axis;
    folding the piece of fabric so that the small truncated branches are superimposed, and
    sewing or binding the small superimposed branches to form a module for protecting a heel, the large branches being configured to be linked in pairs by a connector to form straps for holding the heel protection module.

11. The method according to claim 8 for manufacturing a protection device, the protection device being configured to protect a hand, the method further comprising the steps of:
    cutting out of the strip of fabric a piece of fabric comprising two symmetrical parts in relation to a folding axis;
    folding the piece of fabric so that the two parts are disposed one above the other; and
    sewing or binding to link in pairs superimposed edges of the two parts, such that the protective device comprises edges which are not sewn or bound, the unsewn or unbound edges forming openings which enable a wrist and fingers to be passed therethrough.

12. The method according to claim 1, wherein the support strip is made of polyvinyl chloride.

13. The method according to claim 1, wherein the at least one module is made of silicone gel.

14. The method according to claim 1, wherein the fabric is elastane polyamide.

* * * * *